United States Patent [19]

Chu et al.

[11] Patent Number: 5,344,964
[45] Date of Patent: Sep. 6, 1994

[54] METHOD FOR PREPARING ESTER END-CAPPED POLYALKYLENE ETHER

[75] Inventors: Shiao-Jung Chu, Hsinchu; Fu-Chen Liu, Nan-Tou Shiann; Ching-Tang Lin, Hsinchu; Wen-Fa Lin, Hsinchu; Kuei-Chih Wang, Hsinchu; Sheng-Te Yang, Hsinchu, all of Taiwan

[73] Assignee: Industrial Technology Research Institute, Hsinchu, Taiwan

[21] Appl. No.: 157,957

[22] Filed: Nov. 24, 1993

[51] Int. Cl.$^5$ ........................ C07C 67/24; C08G 59/68
[52] U.S. Cl. ................................. 560/240; 528/408; 528/409; 528/410; 528/411
[58] Field of Search ................ 560/240; 528/408, 409, 528/410, 411

[56] References Cited

U.S. PATENT DOCUMENTS

| | | | |
|---|---|---|---|
| 4,153,786 | 5/1979 | Pruckmayr | 528/408 |
| 4,202,964 | 5/1980 | Pruckmayr et al. | 568/617 |
| 4,214,070 | 7/1980 | Krespan | 528/220 |
| 4,510,333 | 4/1985 | Pruckmayr | 568/617 |
| 4,564,671 | 1/1986 | Mueller | 528/416 |
| 4,568,775 | 2/1986 | Aoshima et al. | 568/617 |
| 4,728,722 | 3/1988 | Mueller | 528/413 |
| 4,803,299 | 2/1989 | Mueller | 560/240 |
| 5,210,283 | 5/1993 | Kahn et al. | 264/60 |
| 5,262,562 | 11/1993 | Hollingsworth et al. | 560/240 |

*Primary Examiner*—Arthur C. Prescott
*Attorney, Agent, or Firm*—Darby & Darby

[57] ABSTRACT

A method for preparing ester end-capped polyalkylene ether is disclosed. Cyclic ether monomers are subjected to ring-opening polymerization at a temperature of 10°–80° C. and a pressure of 0–10 atm in the presence of a solid acid of a mixed oxide of group III and group IV elements serving as catalyst and a mixture of acid and acid anhydride serving as molecular weight moidifier. The group III and group IV elements used should have a Ho index of +3.0 to −10.0.

15 Claims, No Drawings

METHOD FOR PREPARING ESTER END-CAPPED POLYALKYLENE ETHER

BACKGROUND

The present invention relates to a method for preparing ester end-capped polyalkylene ether. In particular, it relates to a method for preparing ester end-capped polyalkylene ether by ring-opening polymerization of cyclic ether in the presence of a solid acid of a mixed oxide of group III and group IV elements as a catalyst and a mixture of acid and acid anhydride as a molecular weight modifier.

Ester end-capped polyalkylene ethers are very important intermediates for industrial applications which can be converted to polyether glycols by hydrolysis or alcoholysis. Polyether glycols are used as a starting material for plastic elastomers such as polyurethanes, and spandex fibers. Due to their superelasticity, superior chemical resistance, and air permeability, they have been extensively used in the manufacture of flexible, air ventilating clothes; panty hose; impact resistant motor parts; adhesives; paints; artificial organs; and artificial blood vessels.

Conventional manufacturing process for polyether glycols involves polymerizing cyclic ether into corresponding acid anion end-capped polyethers by the ring-opening process in the presence of a strong liquid acid as the catalyst, followed by subjecting them to hydrolysis or alcoholysis to form hydroxy group end-capped polyether glycols. For example, U.S. Pat. No. 4,510,333 and EP 0167292 A1 disclose a method in which tetrahydrofurans are polymerized into flurosulfonic radical end-capped polyethers by the ring-opening process in the presence of fluorosulfonic acid as a catalyst. U.S. Pat. No. 3,712,430 and Japan Patent No. Sho 45-13940 disclose the same method but fuming sulfuric acid and perchloric acid are respectively used as catalysts instead of flurosulfonic acid. One disadvantage of these methods are that the molecular weight distribution of the resulting polyether is rather broad, the number average molecular weight ranges from 500 to several ten thousands and the molecular distribution ($\overline{Mw}/\overline{Mn}$) is much greater than 2. Another disadvantage of this method is that the liquid acid catalyst used can not be recycled for reuse because it is very difficult to separate from the product prior to the hydrolysis or alcoholysis reactions. This leads to the consumption of a large amount of energy. Furthermore, the corrosion of reaction vessels, and the need of sequential treatment of waste acid require a great deal of labour and cost.

U.S. Pat. Nos. 4,153,786 and 4,202,964 and German Patent GB 2025995 disclose a new process which involves carrying out ring-opening polymerization in the presence of a cationic ion exchange resin bearing —SO$_3$H groups as a catalyst and an acetic anhydride as a precursor. However, since the water content of the catalyst must be strictly limited, the raw material tetrahydrofurans must be predehydrated to contain less than 100 ppm of water. Furthermore, as the cationic ion exchange resin used is normally poor-heat resistant, there are difficulties when a regeneration is desired.

U.S. Pat. Nos. 4,564,671, 4,728,722 and 4,803,299 disclose a process for the preparation of polytetramethyl ether acetate(PTMEA), which uses a acidic clay or a zeolite as catalyst and acetic anhydride as promoter. The disadvantage to this process is that the molecular weight distribution of the resulting PTMEA is relatively broad, and the $\overline{Mw}/\overline{Mn}$ is about 3.0.

U.S. Pat. No. 4,568,775, Japan Patent Nos. Sho 63-30931, 63-30930, and laid-open Patent Nos. Sho 61-268787 60-158218 disclose a process for directly producing polyether glycols by using a heteropoly-acid as a catalyst. The process can synthesize polyether glycols in a single step, however, as the heteropoly-acid catalyst is readily soluble, it will remain in and stain the final products, and therefore requires of further treatment of the final product. Furthermore, the yield of this process is rather low, usually less than 10%.

SUMMARY OF THE INVENTION

An object of the present invention is therefore to provide a method for preparing ester end-capped polyalkylene ether in which polymers having a narrower molecular weight distribution and a number average molecular weight between 500 and 5000 can be obtained; the separation of the catalyst can be readily effected, enabling recycling of them and preventing corrosion of the equipment; and the yield can be raised to above 30%.

It has been found by the inventors that the above object can be attained if cyclic ethers having 3 to 6 carbon atoms are polymerized in the presence of a solid acid of a mixed oxide of group III and group IV elements serving as a catalyst, and a mixture of acid and acid anhydride serving as a molecular weight modifier, at a temperature of 10°-80° C. and a pressure of 0-10 atm.

According to one aspect of the method of the invention, the raw material, cyclic ethers having 3 to 6 carbon atoms do not require special treatment to remove the water they contain because the solid acid catalyst of the invention has high water endurance.

The present invention can be more fully understood by reading the subsequent detailed description and examples.

DETAILED DESCRIPTION OF THE INVENTION

According to the method of the invention, cyclic ethers having 3 to 6 carbon atoms are suitable for use as raw material. Preferred cyclic ethers are those having the following formula:

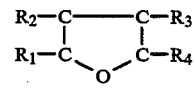

wherein R$_1$, R$_2$, R$_3$ and R$_4$ are alkyl group having 1-4 carbon atoms. Tetrahydrofurans are the most preferred cyclic ethers. Normally used tetrahydrofurans which contain about 400 ppm of water, or even industrial-grade tetrahydrofurans which contain about 800 ppm of water, can also be used for monomers of the ring-opening polymerization of the invention.

The solid acid catalysts used according to the present invention are mixed oxides of group III and group IV elements. Note that the group III and group IV elements should have a Ho (Hamelt) index ranging from +3.0 to −10.0. Examples of suitable oxides include zirconium dioxide, zinc oxide, silicon oxide, titanium dioxide, aluminum oxide, ferric oxide, molybdenum trioxide, chromium oxide, and tungsten oxide. The mixed oxides can be a mixture of two or at least two of the above oxides. Preferred combinations are silicon oxide-titanium dioxide, silicon oxide-aluminum oxide, silicon oxide-zirconium dioxide, molybdenum trioxide-zirconium dioxide and tungsten trioxide-zirconium dioxide. The mixed oxides are prepared by coprecipitating solutions or oxides of aluminum, silicon, iron, zirconium, titanium, molybdenum or tungsten and then fabricating and calcining to form pellets. Alternatively, oxides of the above III or IV elements are immersed in a solution of other oxides and then fabricated and calcined to form pellets. If the mixed oxides are composed of two oxides, the molar ratio of the two oxides should be in the range of 100/1–1/100, preferably in the range of 50/1–1/50. If a third oxide is added, the amount of the third oxide should be 0–30 percent by weight, preferably 0–20 percent by weight, based on the total amount of the mixed oxides. The mixed oxides are preferably fabricated and calcined at a temperature of 400°–1200° C. with the introduction of air to form 0.2 cm×0.3 cm pellets.

The ring-opening polymerization according to the invention can be carried out batchwise by using a slurry reactor or continuously by using a fixed-bed reactor.

If a batchwise slurry reactor is used, the amount of the catalysts should be 5–40 percent by wieght, preferably 10–25 percent by weight based on the cyclic ethers. If the amount of the catalyst is less than 5 percent by weight, the time for polymerization is lengthened. On the other hand, if the amount exceeds 40 percent by weight, it is no help to the reaction. The amount of the mixture of acid and acid anhydride should be 1–20 percent by weight, preferably 2–15 percent by weight based on the cyclic ethers. The molar ratio of the acid and acid anhydride should be 15/1 to 1/15, preferably 10/1 to 1/10. The ring-opening polymerization is carried out at a temperature of 10°–80° C., more preferably between 20°–60° C. for at least 90 minutes. The reaction pressure is preferably from 0–10 atm, more preferably from 1–10 atm. After the completion of the polymerization, the catalyst is filtered and recovered, and the formed ester end-capped polyalkylene ether, after separation from unreacted cyclic ether, is sequentially subjected to hydrolysis or alcoholysis to produce polyether glycols. The separated cyclic ethers can be recycled for use. Note that, according to the invention, the recovered catalysts can be reused without further treatment.

If a fixed-bed reactor is used for the ring-opening polymerization, the operation conditions are substantially the same as that of the batchwise slurry reactors. In this case, the catalyst can be reused directly without filtration and separation steps, and the formed ester end-capped polyalkylene ether can be directly collected, thereby rendering the operation more efficiently. The cyclic ethers, acids and acid anhydrides can be fed to the reactor by using a mixed feed method at a rate of 0.005–5 hr$^{-1}$, preferably 0.1–2 hr$^{-1}$.

The examples which follow illustrate the method according to the invention without implying any limitation. In these examples, tetrahydrofurans(THF) is used as raw material. For batchwise slurry reaction, a 300 ml jacket glass reactor is used and the catalyst is pulverized into particles capable of passing through a 40 to 80 mesh. The reaction conditions and the amount of catalysts are set forth in the examples. For continuous fixed-bed reaction, a one inch glass tube is used as a reactor and 50 ml mixed oxides in the form of 0.2 cm×0.3 cm particles are added as the catalyst. Unreacted tetrahydrofurans are recovered by reduced distillation after the product is condensed and collected. The number average molecular weight and weight average molecular weight of the produced polytetramethylene ether acetate is measured by gel permeation chromatography. Yield and molecular weight distribution are calculated respectively by the following equations.

$$\text{yield}(\%) = \frac{\text{weight of polytetramethylene ether acetate}}{\text{weight of cyclic ether in the feed}} \times 100\%$$

$$\overline{Mw}/\overline{Mn} = \frac{\text{weight average molecular weight}}{\text{nummber average molecular weight}} \times 100\%$$

EXAMPLE 1

To 1 liter of distilled water, 202.39 g of zirconium oxychloride($ZrOCl_2.8H_2O$) was added, stirred to form a solution. 10 percent by weight of ammonia water was dropwise added into the solution and the pH value was adjusted to 10. A white precipitate was formed, filtered, washed and dried for use.

The white precipitate was then dissolved in a 100 ml solution of molybdenum acid for 24 hours, then filtered, dried and extruded into pellets of 0.2 cm×0.3 cm. The pellets was subsequently calcined at 800° C. for 5 hours with the introduction of air. 48.3 g of catalyst was obtained.

The obtained catalyst was pulverized into 20–40 mesh. 25 g of the pulverized catalyst was placed in a slurry reactor as mentioned above, 100 g of tetrahydrofuran, 5 g of acetic anhydride and 2 g of acetic acid were added. The temperature of the reactor was raised to 40° C. and reacted for 5 hours. After the completion of the reaction, the catalyst was removed from the mixture by filtration, and the unreacted tetrahydrofuran was recovered by reduced distillation. Polytetramethylene ether acetate with a number average molecular weight of 1223 and a $\overline{Mw}/\overline{Mn}=1.98$ was obtained. The yield is 58.2%.

EXAMPLE 2

To 300 ml ethanol, zirconium butanate $Zr(OC_4H_9)_4$ (46.84 g) and tetraacetic silicate($Si(OC_2H_5)_4$)(183.09 g) were added, and stirred to form a mixed solution of zirconium and silicon. 10 percent by weight of ammonia water was dropwise added to the mixed solution while stirring. The pH value of the mixed solution was adjusted to 10 and a white precipitate was obtained. The white precipitae was filtered, washed, dried and fabricated into pellets of 0.2 cm×0.3 cm by an extruder. The pellets was then calcined at 600° C. for 8 hours with the introduction of air. 64.84 g of catalyst was obtained.

The obtained catalyst was pulverized into 40–80 mesh. 15 g of the pulverized catalyst was placed in a slurry reactor as mentioned above, 100 g of tetrahydrofuran, 3 g of acetic anhydride and 1 g of acetic acid were added. The temperature of the reactor was raised to 50° C. and reacted for 90 minutes. After the completion of the reaction, the catalyst was removed from the mixture by filtration, and the unreacted tetrahydrofuran was recovered by reduced distillation. Polytetramethylene ether acetate with a number average molecular weight of 1927 and a $\overline{Mw}/\overline{Mn}=1.89$ was obtained. The yield was 29%.

COMPARATIVE EXAMPLE 1

Polysiloxane-sulfonic acid (25 g), tetrahydrofuran (100 g), acetic anhydride (5 g) and acetic acid (2 g) were placed in the slurry reaction, and the temperature of the reactor was raised to 40° C. for 3.5 hours. After filtration and separation of the catalyst, polytetramethylene ether glycol with a number average molecular weight of 1310 and a $\overline{Mw}/\overline{Mn}=2.0$ was obtained (yield=9.2%).

EXAMPLE 3

To 100 ml solution of 5.15 g zirconium oxychloride, silicon oxide (50 g, T-1571 Girdler, Japan) was added. The immersion lasted for 3 hours. After evaporation, the residues was calcined at 500° C. for 6 hours. 52 g catalyst was obtained. 50 ml of the catalyst was placed in a fixed-bed tube reactor, and a solution of tetrahydrofuran, acetic anhydride and acetic acid( molar ratio=100:8:1) was introduced into at a flow rate of 0.1 hr$^{-1}$ by using a high pressure pump, and allowed to contact react at 45° C. and 1 atm. The product was collected and analyzed to have a number average molecular weight of 1210 and a $\overline{Mw}/\overline{Mn}=1.930$. The yield was 34%.

EXAMPLE 4

To 300 ml ethanol, 98.3 g of tetraacetic silicate and 107.6 g of titanium isopropanate were added, stirred to form a solution of silicon and titanium. 10 percent by weight of ammonia water was dropwise added to the solution and the pH value was adjusted to 10. A white precipitate was formed, filtered, washed, dried, and extruded into pellets of 0.2 cm×0.3 cm. The pellets were then calcined at 1000° C. for 3 hours with the introduction of air. 64.3 g of catalyst was obtained.

The obtained catalyst was pulverized into 40–80 mesh. 20 g of the pulverized catalyst was placed in a slurry reactor, 100 g of tetrahydrofuran, 8 g of acetic anhydride and 1 g of acetic acid were added. The temperature of the reactor was raised to 45° C. and reacted for 90 minutes. After filtration and separation unreacted tetrahydrofuran by reduced distillation, polytetramethylene ether acetate was obtained. The properties of the resultant polymer are listed in Table 1.

EXAMPLE 5

The same procedures as Example 1 were repeated except that 50 g of mixed precipitate of silicon hydroxide and titanium hydroxide and 8.65 g of $(NH_4)_6H_2W_{12}O_{40}$ were used. 41.3 g of catalyst was obtained. The properties of the resultant polymer are listed in Table 1.

EXAMPLE 6

The same procedures as Example 2 were repeated except that zirconium butanate was replaced by 72.0 g of zirconium oxychloride, tetraacetic silicate was replaced by 100.7 g of silica sol(Ludox, As grade) and 300 ml of ethanol was replaced by distilled water. The properties of the resulting polymer are listed in Table 1.

EXAMPLE 7

The same procedures as Example 6 were repeated except that zirconium oxychloride was replaced by 24.7 g of aluminum nitrate and 148.3 g of silica sol was used. 62.7 g of catalyst was obtained. The properties of the resulting polymer are listed in Table 1.

EXAMPLE 8

The same procedures as Example 6 were repeated except that 4.1 g of zirconium oxychloride and 471.5 g of aluminum nitrate were used. the properties of the resulting polymer are listed in Table 1.

EXAMPLE 9

Precipitate of zirconium hydroxide and aluminum hydroxide was prepared by the same procedures as in Example 8. After filtration and washing, 100 g of the precipitate was dissolved in 100 ml aqueous solution of 2 g boric acid for 24 hours. After evaporation and calcination at 600° C. for 5 hours, 82 g of catalyst was yielded. Polymerization was carried out according to the same procedures as in Example 1. The properties of the resultant polymer are listed in Table 1.

COMPARATIVE EXAMPLE 2

50 g of white powder of zirconium hydroxide of Example 1 was filtered, fabricted and calcined at 550° C. with the introduction of air for 6 hours. 38 g of catalyst was obtained. The catalyst was then pulverized to particles of 40–80 mesh. 25 g of the particles were placed in a slurry reactor and 100 g of tetrahydrofuran, 5 g of acetic anhydride, and 2 g of acetic acid were added, reacted at 40° C. for 5.0 hours. The properties of the resultant polymer are listed in Table 1.

COMPARATIVE EXAMPLE 3

50 g of hetropoly-acid catalyst, $H_2PW_{12}O_{40}.1.39H_2O$ was placed in a slurry reactor and 100 g of tetrahydrofuran was added, and allowed to react at 40° C. for 4 hours. The properties of the resultant polymer are listed in Table 1.

COMPARATIVE EXAMPLE 4

50 g of hetropoly-acid catalyst, $H_4SiMo_{12}O_{40}.1.5H_2O$ was placed in a slurry reactor, 100 g of tetrahydrofuran 5 g of acetic anhydride and 2 g of acetic acid were added, and allowed to react at 40° C. for 3.5 hours. The properties of the resultant polymer are listed in Table 1.

COMPARATIVE EXAMPLE 5

50 g of hetropoly-acid catalyst, $H_4SiW_{12}O_{40}.3.45H_2O$ was placed in a slurry reactor, 100 g of tetrahydrofuran was added, and allowed to react at 40° C. for 4 hours. The properties of the resultant polymer are listed in Table 1.

EXAMPLE 10

Same catalyst as in Example 1 was used but the reaction temperature was changed to 25° C. and the reaction time was 2.0 hours. The yield was 34.3%. The product, polytetramethylene ether glycol had a number average molecular weight of 3980 and a $\overline{Mw}/\overline{Mn}$ of 1.73 and was colorless.

TABLE 1

| No. | catalyst (g) | acetic anhydride (g) | acetic acid (g) | rex tem. °C. | rex time hr | yield % | $\overline{Mn}$ | $\overline{Mw}/\overline{Mn}$ |
|---|---|---|---|---|---|---|---|---|
| Exp. | | | | | | | | |
| 1 | 25 | 5 | 2 | 40 | 5 | 58.2 | 1223 | 1.98 |
| 2 | 15 | 3 | 1 | 50 | 1.5 | 29.0 | 1162 | 1.89 |
| 4 | 20 | 8 | 1 | 45 | 1.5 | 31.6 | 1032 | 1.95 |
| 5 | 25 | 5 | 2 | 40 | 1.5 | 29.1 | 1231 | 1.95 |
| 6 | 15 | 3 | 1 | 50 | 1.5 | 35.2 | 1140 | 1.92 |
| 7 | 15 | 3 | 1 | 50 | 1.5 | 37.8 | 1184 | 1.78 |
| 8 | 15 | 3 | 1 | 50 | 1.5 | 28.7 | 1210 | 1.93 |
| 9 | 25 | 5 | 2 | 40 | 5 | 36.4 | 1378 | 1.82 |
| comp. Exp. | | | | | | | | |

TABLE 1-continued

| No. | cata-lyst (g) | acetic anhydride (g) | acetic acid (g) | rex tem. °C. | rex time hr | yield % | Mn | $\overline{Mw}/\overline{Mn}$ |
|---|---|---|---|---|---|---|---|---|
| 1 | 25 | 5 | 2 | 40 | 3.5 | 9.2 | 1310 | 2.0 |
| 2 | 25 | 5 | 2 | 40 | 5 | 7.8 | 1320 | 2.0 |
| 3* | 50 | 0 | 0 | 40 | 4 | 7.2 | 1178 | 1.81 |
| 4* | 50 | 5 | 2 | 40 | 3.5 | 2.8 | 1045 | 1.92 |
| 5* | 50 | 0 | 0 | 40 | 4 | 2.9 | 930 | 1.83 |

* the products are yellow in color

It can be seen from the above Table 1 that the polytetramethylene ether glycols prepared by the method of the invention have superior ring-opening polymerization activity when compared to the conventional methods which use ion exchange resin bearing —$SO_3H$ groups or hetropoly-acid as the catalyst. The polyether glycols prepared by the method of the invention have superior quality, are colorless, require no further treatment, and also have a narrower molecular weight distribution with a $\overline{Mw}/\overline{Mn}$ between 1.8-2.0. The products produced by using hetropoly-acid as catalyst are yellowish in color and therefore need to be subjected to purification treatment.

EXAMPLE 11

The same catalyst as in Example 2 was used, but 2 g of acetic anhydride and 2 g of acetic acid were used. The polymerization was took place at 50° C. for 1.5 hours. The produced polytetramethylene ether glycols have a number average molecular weight of 1623, a $\overline{Mw}/\overline{Mn}$ of 1.99 and are colorless. The yield was 30.3%.

EXAMPLE 12

The same catalysts as in Example 2 were used, but 1 g of acetic anhydride and 5 g of acetic acid were used. The polymerization was took place at 50° C. for 1.5 hours. The produced polytetramethylene ether glycols have a number average molecular weight of 1470, a $\overline{Mw}/\overline{Mn}$ of 1.94 and are colorless. The yield was 27.4%.

EXAMPLE 13

The same catalysts as in Example 2 were used, but instead, 10 g was used, and 15 g of acetic anhydride and 5 g of acetic acid were used. The polymerization took place at 60° C. for 1 hour. The produced polytetramethylene ether glycols have a number average molecular weight of 620, a $\overline{Mw}/\overline{Mn}$ of 1.94 and are colorless. The yield was 35.2%.

EXAMPLE 14

The same procedures of Example 2 were repeated except that an industrial grade tetrahydrofuran was used. The produced polyetetramethylene ether glycol had a number average molecular weight of 1108, a $\overline{Mw}/\overline{Mn}$ of 1.85 and was colorless. The yield was 30.1%.

EXAMPLE 15

The same catalyst as in Example 6 was used, but 1.5 g of acetic anhydride and 1.0 g of acetic acid were used. The polymerization took place at 30° C. for 2 hours. The produced polytetramethylene ether glycol had a number average molecular weight of 2870, a $\overline{Mw}/\overline{Mn}$ of 1.87 and was colorless. The yield was 26.7%.

EXAMPLE 16

A catalyst recovered from Example 15 was used in this example. Tetrahydrofuran containing 400 ppm water, 2.5 g of acetic aicd and 5 g of acetic anhydride were used, and allowed to react at 40° C. for 1.5 hours. A colorless polytetramethylene ether glycol with a number average molecular weight of 1264 and a $\overline{Mw}/\overline{Mn}$ of 1.80 was obtained. The yield was 36.6%.

EXAMPLE 17

A catalyst recovered from Example 16 was used and the same reaction conditions as in Example 16 were repeated. The obtained polytetramethylene ether glycols had a number average molecular weight of 1284 and a $\overline{Mw}/\overline{Mn}$ of 1.87, and was colorless. The yield was 34.1%.

EXAMPLE 18

A catalyst recovered from Example 17 was used and the same reaction conditions as in Example 17 were repeated. The obtained polytetramethylene ether glycols had a number average molecular weight of 1235 and a $\overline{Mw}/\overline{Mn}$ of 1.89, and was colorless. The yield was 33.5%.

EXAMPLE 19

The same procedures as in Example 3 were repeated except that the composition of the catlayst was changed to zirconium oxychloride 720 g and silica sol 100 g. After precipitating with ammonia water, washing with water, dring, fabricating and calcining at 500° C. with introduction of air for 10 hours, the catalyst was obtained. The catalyst was placed in a glass tube reactor and a mixed solution of tetrahydrofuran, acetic anhydride and acetic acid was introduced into the reactor by using a high pressure pump at a rate of 3 hr$^{-1}$ and contact reacted with the catalyst at 60° C. at a pressure of 5 atm. The molar ratio of tetrahydrofuran: acetic anhydride: acetic acid was 100:5:2. Condensation and collection gave a colorless polytetramethylene ether glycol having a number average molecular weight of 1185, a $\overline{Mw}/\overline{Mn}$ of 1.84. The yield was 37.3%.

EXAMPLE 20

The same procedures as Example 19 were repeated except that the liquid feed was changed to a mixed solution of tetrahydrofuran, 2-isobutyltetrahydrofuran, acetic anhydride, and acetic acid with a molar ratio of 100:50:8:3, and the mixed solution was introduced into the reactor by a high pressure pump at a flow rate of 3.0 hr$^{-1}$ and contact reacted with the catalyst at 45° C. in 1 atm. Condensation and collection gave a polybutylether glycol having a number average molecular weight of 1432 and a $\overline{Mw}/\overline{Mn}$ of 1.93. The product was colorless.

What is claimed is:
1. A method for preparing ester end-capped polyalkylene ether, comprising the following steps:
   a) providing a cyclic ether having 3 to 6 carbon atoms;
   b) oligomerically polymerizing said cyclic ether, at a temperature of 10°-80° C. and a pressure of 0-10 atm in the presence of a solid acid of a mixed oxide of group III and group IV elements serving as a catalyst and a mixture of acid and acid anhydride serving as molecular weight modifier, wherein said group III and group IV element have a Ho index of +3.0 to −10.0; and c) separating the resulting ester end-capped polyalkylene ether from the catalyst.

2. The method as claimed in claim 1, wherein the cyclic ether is a tetrahydrofuran derivative of the following formula:

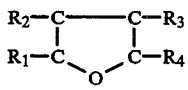

wherein $R_1$, $R_2$, $R_3$ and $R_4$ are alkyl groups of 1 to 4 carbon atoms.

3. The method as claimed in claim 2, wherein said tetrahydrofuran derivative is tetrahydrofuran.

4. The method as claimed in claim 2, wherein said tetrahydrofuran is 2-isobutyl tetrahydrofuran.

5. The method as claimed in claim 1, wherein the amount of the catalyst is 5–40 percent by weight of the cyclic ether.

6. The method as claimed in claim 5, wherein the amount of the catalyst is 10–25 percent by weight of the cyclic ether.

7. The method as claimed in claim 1, wherein the mixed oxide is a mixture of at least two oxides, each oxide is selected from the group consisting of zirconium dioxide, zinc oxide, silicon oxide, titanium dioxide, aluminum oxide, ferric oxide, molybdenum trioxide, chromium oxide and tungsten trioxide.

8. The method as claimed in claim 7, wherein the mixed oxide is a mixture of two oxides, each oxide is selected from the group consisting of zirconium dioxide, zinc oxide, silicon oxide, titanium dioxide, aluminum oxide, ferric oxide, molybdenum trioxide, chromium oxide and tungsten trioxide, and the molar ratio of the two oxides is between 100/1 and 1/100.

9. The method as claimed in claim 7, wherein the molar ratio of the two oxides is between 50/1 and 1/50.

10. The method as claimed in claim 1, wherein the amount of the molecular weight modifier is 1–20 percent by weight of the cyclic ether.

11. The method as claimed in claim 10, wherein the amount of the molecular weight modifier is 2–15 percent by weight of the cyclic ether.

12. The method as claimed in claim 1, wherein the molecular weight modifier is a mixture of acid anhydride having 3–5 carbon atoms and acid having 3–5 carbon atoms.

13. The method as claimed in claim 12, wherein the molecular weight modifier is a mixture of acetic acid and acetic anhydride.

14. The method as claimed in claim 1, wherein the cyclic ether is polymerized at a temperature of 20°–60° C.

15. The method as claimed in claim 1, wherein the cyclic ether is polymerized at a pressure of 1–10 atm.

* * * * *